United States Patent [19]

Gregory et al.

[11] Patent Number: 5,649,923

[45] Date of Patent: *Jul. 22, 1997

[54] CATHETER DEVICES FOR DELIVERING LASER ENERGY

[75] Inventors: Kenton W. Gregory, Boston; R. Rox Anderson, Somerville, both of Mass.

[73] Assignee: The General Hospital Corporation, Boston, Mass.

[*] Notice: The term of this patent shall not extend beyond the expiration date of Pat. No. 5,304,171.

[21] Appl. No.: 225,259

[22] Filed: Apr. 8, 1994

Related U.S. Application Data

[63] Continuation of Ser. No. 261,838, Oct. 24, 1988.

[51] Int. Cl.$^6$ .................................................. A61B 17/36
[52] U.S. Cl. ................................ 606/15; 606/7; 606/14
[58] Field of Search .......................... 606/2–19; 385/125, 385/31, 33, 142, 123, 128

[56] References Cited

U.S. PATENT DOCUMENTS

| | | | |
|---|---|---|---|
| 3,995,934 | 12/1976 | Nath | 385/125 |
| 4,045,119 | 8/1977 | Eastgate | 385/125 |
| 4,201,446 | 5/1980 | Geddes et al. | 385/125 |
| 4,207,874 | 6/1980 | Choy | 606/7 |
| 4,657,014 | 4/1987 | Edelman et al. | |
| 4,697,870 | 10/1987 | Richards | 385/125 X |
| 4,747,405 | 5/1988 | Leckrone | 606/15 X |
| 4,850,351 | 7/1989 | Herman et al. | 606/7 |
| 4,911,712 | 3/1990 | Harrington | 606/14 |
| 4,927,231 | 5/1990 | Levatter | 385/125 X |
| 5,026,367 | 6/1991 | Leckrone et al. | 606/7 |
| 5,030,217 | 7/1991 | Harrington | 606/14 |
| 5,061,265 | 10/1991 | Abela et al. | 606/7 |
| 5,246,436 | 9/1993 | Rowe | 606/16 |
| 5,267,341 | 11/1993 | Shearin | 606/16 |
| 5,304,171 | 4/1994 | Gregory et al. | 606/16 |

FOREIGN PATENT DOCUMENTS

247746  12/1987  European Pat. Off. ................. 606/7

*Primary Examiner*—Lee S. Cohen
*Assistant Examiner*—Michael Peffley
*Attorney, Agent, or Firm*—Stetina Brunda & Buyan

[57] ABSTRACT

A method for conducting laser energy to a site includes steps of bringing the proximal end of a flexible tube near the site, filling at least a proximal portion of the tube with a liquid by introducing the liquid into the tube, allowing a portion of the liquid to flow out from the proximal end of the tube toward the site, and directing laser energy from a laser energy source into the distal end of the tube, whereby a portion of the laser energy emerges from the proximal end of the tube at the site. Also, such a method in which the liquid is a radiographic contrast medium. Also, such a method for removing an obstruction from a blood vessel in an animal. Also, apparatus for delivering laser energy to a site includes a flexible tube, a liquid, the tube having an opening in a first end through which the liquid can pass, means for providing a flow of the liquid into the tube, and a source of laser energy operationally associated with a second end of the tube, wherein the tube and the liquid are adapted to cooperate, when the tube contains the liquid, to conduct laser energy from the source and to emit a portion of the laser energy from the first end of the liquid-containing tube.

28 Claims, 4 Drawing Sheets

CATHETER DEVICES FOR DELIVERING LASER ENERGY

This patent application is a continuation of copending U.S. patent application Ser. No. 07/261,838, which was filed on Oct. 24, 1988.

BACKGROUND OF THE INVENTION

This invention relates to conducting laser energy from a laser energy source along a course that includes curves of small radius.

In many circumstances in various industrial and medical applications, matter to be cut or welded or otherwise altered or removed is located at a site that is inaccessible or difficult to reach.

Many sites within the body of an animal such as a human patient are difficult to reach for performing surgery, because they are surrounded by hard tissues such as bone or because they are surrounded by delicate tissues which can be damaged. Sites within the thorax, such as the heart and the blood vessels near it, for example, are enclosed by bone structures, and sites within the cranium, such as arteries supplying the brain, for example, are surrounded by delicate brain tissue as well as by bone. The coronary arteries and the arteries of the brain can become occluded for example by atheromatous plaque formations or by thrombi or emboli, with serious consonances for the patient.

One approach to providing a supply of blood to the heart when a coronary artery is occluded is bypass surgery, that is, coronary artery bypass. The patient's thorax is opened, and a substitute conduit for supplying blood to the heart is provided by engrafting a substitute vessel between a point upstream from the occlusion, such as the aorta, and a point in the coronary artery downstream from the occlusion. Coronary bypass surgery is an involved and delicate procedure, entailing significant risk and expense to the patient. Many patients are unable to benefit from bypass surgery.

In an alternative approach to relieving an occlusion of an artery, drugs are administered to cause the vessels to dilate. Not all patients can use such drugs, however, and the results are generally only temporary, as the occluding process can continue, eventually blocking even the dilated vessel.

In still other approaches, generally termed percutaneous translumenal angioplasty, an instrument for dilating the occluded artery is introduced, generally by means of a catheter, through an opening in the skin and through an opening in the wall of a large artery such as the brachial artery or the femoral artery, and passed within the arterial lumens to the site of the occlusion. In balloon angioplasty, for example, a fine guide wire is first passed to the site of the occlusion through the lumens of major arteries, observed by radiography as it progresses; then a catheter having a balloon near its tip is passed over the wire to the site, also within the arterial lumens; and finally the balloon is inflated at the site of the occlusion to stretch the walls of the artery and open the lumen. The results of balloon angioplasty can also be temporary, as the occluding process in 30–40% of patients can continue at the site until the vessel is again blocked. Moreover, the procedure carries risks of perforation or acute occlusion of the arteries by the instrument, and the flow of blood through the vessel being treated is interrupted for a time during the procedure. Only selected patients can benefit from balloon angioplasty, leaving many patients with no viable treatment, including patients having atheromas involving long segments of vessels, or having diffuse distal artery disease, or having arteries too tortuous to permit passage of guidewires.

In a variety of industrial and medical applications, useful results can be obtained by directing laser energy at a site. For example, various materials melt or vaporize upon absorption of laser energy, and parts constructed of such materials can in effect be cut or welded to achieve a desired result. Laser energy can be used in surgery for alteration or removal of tissues or obstructions or deposits by directing the energy at the matter to be altered or removed.

In a surgical technique known as laser angioplasty, conventional light guides using fiber optics have been employed for directing laser energy onto arterial plaque formations to ablate the plaque and remove the occlusion. Individual optically conducting fibers are typically made of fused silica or quartz, and are generally fairly inflexible unless they are very thin. A thin fiber flexible enough to pass through a course having curves of small radius, such as through arterial lumens from the femoral or the brachial artery to a coronary artery, typically projects a beam of laser energy of very small effective diameter, capable of producing only a very small opening in the occlusion; moreover the energy is attenuated over relatively small distances as it passes within a thin fiber. Small diameter fibers can tend to mechanically perforate vessels when directed against the vessel wall as they are passed within the vessel toward the site.

In order to bring a sufficient quantity of energy from the laser to the plaque, light guides proposed for use in laser angioplasty usually include a number of very thin fibers, each typically about 100 to 200 microns in diameter, bundled together or bound in a tubular matrix about a central lumen, forming a catheter. Laser energy emerging, from a small number of fibers bundled together in known such catheters produces lumens of suboptimal diameter which can require subsequent enlargement by, for example, balloon dilation. Such devices do not remove an adequate quantity of matter from the lesion, and their uses are generally limited to providing access for subsequent conventional balloon angioplasty.

Moreover, although individual fibers of such small dimensions are flexible enough to negotiate curves of fairly small radius, a bundle of even a few such fibers is much less flexible, and use of laser angioplasty has as a practical matter been limited to the larger, straighter blood vessels such as, for example, the large arteries of the leg, in which the laser energy is conducted by the light guide over only relatively short distances on a relatively straight course. Coupling mechanisms for directing laser energy from the source into the individual fibers in a light guide made up of multiple small fibers can be complex, including lenses and mechanisms by which the individual fibers can be addressed serially by the source beam. Improper launch of the laser energy into such a light guide can destroy the fibers, ruining the instrument and endangering the patient.

More flexible light guides can be provided by filling a flexible tube with a liquid material whose refractive index is less than that of the tube wall material. H. F. Eastgate, U.S. Pat. No. 4,045,119, describes a liquid core light guide, having a plug at each end of the tube to seal the liquid in, for transmitting laser energy at high power from a laser source such as a pulsed laser to an area of application.

The presence of blood near the distal end of such instruments can prevent laser light from reaching its appropriate target, such as for example arterial plaque or a blood clot. Moreover, absorption of laser energy by blood or blood components can result in generation of heat or formation of detonations, which can damage adjacent vessel walls.

SUMMARY OF THE INVENTION

We have discovered that laser energy can be efficiently conducted along a course that includes curves of small radius and directed onto a target at a remote site by launching laser energy into a liquid-filled flexible tube that is at least partially open at the end nearest the site (i.e. the distal end of the tube) so as to permit a portion of the liquid to flow out from that end toward the target.

In general, in one aspect, the invention features a method for conducting laser energy to a site, including the steps of bringing the distal end of a flexible tube near the site, filling the tube with a liquid that can include a radiographic contrast medium, and directing laser energy from a laser energy source into the distal end of the tube, whereby a portion of the laser energy emerges from the distal end of the tube at the site. In some embodiments the tube is provided with means for limiting the flow liquid out from the tube at the distal end.

In another aspect, the invention features a method for conducting laser energy to a site, such as into a site of the body of an animal, including the steps of bringing the proximal end of a flexible tube near the site, providing a flow of a liquid into the tube, and directing laser energy from a laser energy source into the proximal end of the tube, whereby a portion of the laser energy emerges from the distal end of the tube at the site.

In preferred embodiments, a portion of the liquid is permitted to flow out from the distal end of the tube toward the site; the step of bringing the distal end of the tube near the site includes passing it into the body of the animal by way of an opening in the animal, or by direct surgical approach, and includes passing it through the lumen of a passage within the body of the animal, such as through the lumen of a blood vessel of the animal. The site includes a mineral deposit, an atheromatous plaque, an atheroembolus, a thrombus, or a blood clot; the site is located in a body space such as in an artery, in a vein, in a ureter, in a common bile duct, in the trachea, in a bronchus, or in the gastrointestinal tract. The step of providing a flow of a liquid into the tube includes passing the liquid from a source of liquid into the tube by way of a port in the tube wall; the method further includes the step of continuing to pass the liquid into the tube after the tube has been filled with the liquid, whereby a portion of the liquid passes out from the distal end of the tube.

Causing the liquid to flow from a source of liquid in a controlled manner through the tube and distally out from the tube during the treatment can produce a column of liquid between the distal end of the tube and the target, effectively permitting a continuous guide for the laser energy for a short distance beyond the distal end of the tube. A variety of body fluids, such as, for example, blood or urine, have indices of refraction sufficiently low with respect to the liquid in the tube to provide such a light guide effect beyond the proximal end of the tube. Moreover, matter that may interfere with the laser treatment, including substances normally present at the site, such as blood in the case where the site is within a blood vessel, or substances produced at the site as debris during the treatment, can be continually flushed away without interrupting the procedure by the flow of liquid out from the distal end of the tube.

In another aspect, the invention features a method for removing an obstruction from a blood vessel in an animal, comprising bringing the distal end of a flexible tube near the obstruction, filling the tube with a liquid by passing the liquid into the tube, continuing to pass the liquid into the tube after the tube has been filled with liquid, so that a portion of the liquid passes out from the tube at the distal end, and directing laser energy from a source into the proximal end of the tube, whereby a portion of the laser energy emerges from the distal end of the tube and strikes the obstruction. Where the obstruction includes an atheromatous plaque, the method can be one for treating atherosclerosis; where the obstruction includes a thrombus, the method can be one for treating thrombosis or thromboembolism.

The method does not require completely restricting the flow of blood through the vessel being treated, so the procedure can be carried out without haste. Moreover, the flushing action of the liquid flowing out from the tube toward the target can enhance laser energy delivery by removing blood, which can absorb wavelengths of laser energy that can be useful for removal of plaque or thrombus.

In another aspect, the invention features apparatus for delivering laser energy to a site, including a liquid, a flexible tube having an opening in one end, arranged and adapted to be brought near the site, through which the liquid can pass, means for providing a flow of the liquid into the tube, and a source of laser energy operationally associated with another end of the tube, wherein the tube and the liquid contained within it can cooperate to conduct laser energy from the source and to emit a portion of the laser energy from the second end of the tube.

In preferred embodiments, at least a portion of the tube is adapted to be bent without substantial change in cross-sectional shape or without kinking into a curve having a radius of curvature as small as 20 mm, more preferably as small as 10 mm; The tube includes a wall having a refractive index $n_w$, one surface of the wall describing the lumenal surface of the tube, and the liquid has a refractive index $n_f$, wherein $n_f$ is greater than $n_w$; the values of $n_f$ and $n_w$ are such that the ratio $$r_{f,w}=(n_f)/(n_w)$$

is greeter than 1.0, more preferably greater than about 1.05, still more preferably greater than about 1.1; the value of $n_f$ is about 1.46, or at least about 1.46; the value of $n_w$ is about 1.33, or at least about 1.33; the liquid includes a radiographic contrast medium; the liquid is biocompatible; a support layer surrounds the wall; the wall is made of a polymer, preferably a fluorinated polymer, such as tetrefluoroethylene hexafluoropropylene (FEP) or polypentadecafluorooctylacrylate elastomer. A cap is affixed to the first end of the tube; the cap is arranged and adapted to substantially restrict movement of the liquid out from the tube by way of the first end; the cap is configured to provide a smooth and rounded proximal surface; the cap has a bore through it substantially aligned with the axis of the tube, preferably of a diameter sufficiently to permit passage of a guidewire through it, preferably sufficiently small to restrict the flow of the liquid through it, preferably about 500 micrometers, or at least about 500 micrometers; the cap is made of quartz, or of sapphire; the cap has a reflective surface arranged and adapted to direct the laser energy in a direction away from the axis of the tube; The lumen of the tube has a transverse dimension between about 1 mm and 3 mm; the lumen has a substantially circular cross-sectional shape; it has a diameter between about 1 mm and 3 mm. The apparatus further includes a coupler at a the second end of the tube for conducting energy from the source of laser energy to the liquid-containing tube; the coupler comprises a window, a lens, or an optical fiber (preferably inserted into the lumen of the tube); the coupler is made of quartz or fused silica; the means for providing a flow of the liquid into the tube includes a conduit for conducting the liquid between the source and the tube; the tube includes a port intermediate its first and second ends for passing the liquid between the source and the tube; the means for providing a flow of the liquid into the tube further includes a filter to prevent bubbles from moving into the tube.

In other embodiments, the tube wall includes a reflective layer, one surface of which describes the lumenal surface of the wall; preferably the reflective layer is of a reflective polymer or metallized material, such as a material including aluminum or silver, coextruded with or bonded to the lumenal surface of the tubing material.

The liquid-core light guide according to the invention can be made sufficiently flexible to negotiate the small curves commonly encountered in finer arteries such as the coronary arteries, while projecting an effective beam sufficiently broad to remove an occlusion. The tubing for the light guide itself can be simply and inexpensively made by, for example, a continuous extrusion or coextrusion process, and cut for length as required for each particular use. Advancing the light guide through arterial or venous lumens can be facilitated by initially advancing a guidewire along the course to be followed and then advancing the light guide over the guidewise to the target location. Alternatively, a guiding catheter can be emplaced at the origin of the obstructed artery and the light guide can be advanced within the lumen of the guiding catheter. The laser energy source can be coupled to the light guide in a straightforward fashion, presenting few launch complications. The laser energy can be launched directly from the laser through a focusing lens to the light guide or alternatively it can be launched initially into a conventional fiber inserted into the lumen of the light guide at the proximal end.

The liquid and the tube can be made from biocompatible materials. Using a radiographic contrast medium as a liquid permits continuous fluoroscopic imaging of progress throughout the procedure without interruption. Moreover, a light guide containing a radiographic contrast medium can be used with fluoroscopic monitoring to deliver laser energy with precision in nonmedical applications where the site to be treated is accessible only by way of a tortuous pathway, such as, for example, in repair or reconstruction of internal parts of hydraulic apparatus in which the hydraulic fluid is a hazardous material.

DESCRIPTION OF THE PREFERRED EMBODIMENTS DRAWINGS

STRUCTURE AND OPERATION

Figure 1:
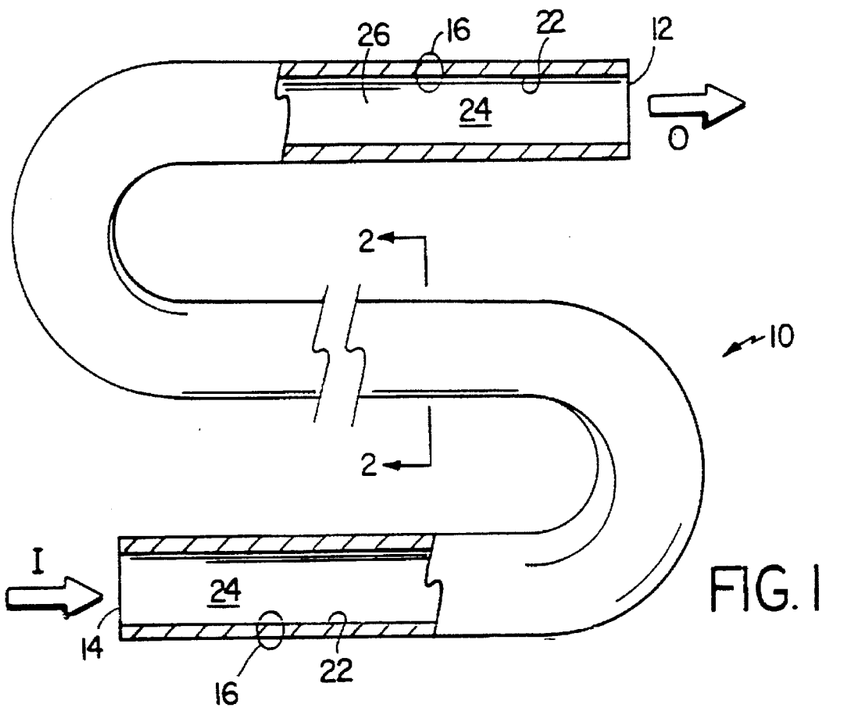
FIG. 1 is a somewhat diagrammatic view of portions of a liquid core light guide according to the invention, partially cut away along the long axis of the tube.
Figure 2:
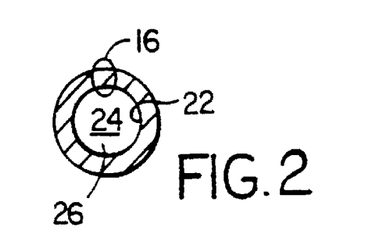
FIG. 2 is a section thru the light guide of FIG. 1 at 2—2.

FIGS. 1 and 2 are views of a liquid core light guide of the invention. The light guide includes a tube, shown generally at 10, whose wall 16 encloses a lumen 24 which is filled with a liquid 26. The inner surface of wall 16 defines lumenal surface 22 of tube 10.

Laser energy can be directed from a source of laser energy (not shown in FIGS. 1 and 2) into proximal end 14 of liquid filled tube 10, as indicated generally by arrow I. The energy passes within the liquid filled tube toward distal end 12. The energy is attenuated as it passes away from the source, so that a portion of it emerges from distal end 12, as indicated generally by arrow O. The proportion of the energy introduced to the proximal end that emerges from the distal end of the liquid-filled light guide depends upon the dimensions and physical characteristics of the liquid and the tube wall, and on the extent to which the tube follows a curving course.

Figure 3:
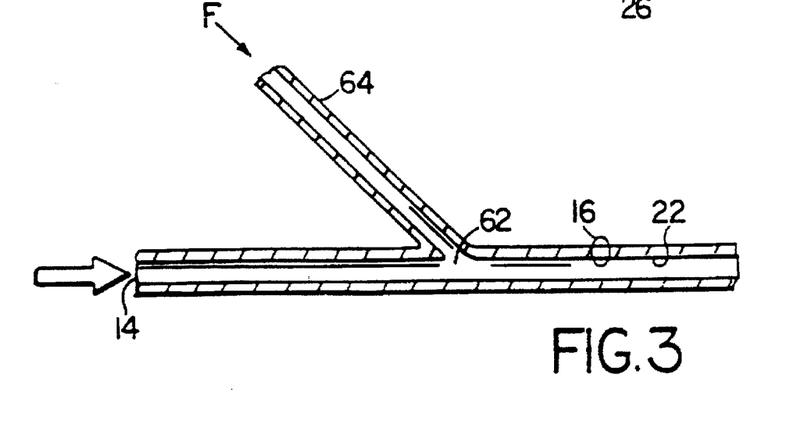
FIG. 3 is a somewhat diagrammatic view of the proximal portion of a liquid core light guide, cut away along the long axis of the tube, showing a liquid port and conduit for passing liquid into the tube.

Referring now to, FIG. 3, port 62 through wall 16 is provided near proximal tube end 14, and one end of conduit 64 is coupled to point 62. Fluid can be introduced at the other end of conduit 64 as indicated by arrow F from a source of liquid such as a syringe or a pump, such as, for example, a peristaltic pump (not shown in FIG. 3), into tube 10 through conduit 64 via port 62. Similarly a conventional guide wire (not shown in FIG. 3) can be introduced into tube 10 through conduit 14 via port 62.

The materials for wall 16 and for liquid 26 are selected in part to provide a high degree of internal reflection at the lumenal surface; that is, wall 16 and liquid 26 are each transparent to the laser energy to be conducted through the light guide, and the index of refraction $n_w$ of wall 16 is less than the index of refraction $n_l$ of liquid 26.

Further, the material for wall 16 is selected in part to provide structural strength as well as flexibility so that the liquid-filled light guide can be bent through curves of small radius without kinking or substantially distorting the cross-sectional geometry of the tube.

Preferably wall 16 is made of a fluorinated ethylenepropylene, such as is available commercially for example as "FEP Teflon®", and the liquid is a radiographic contrast medium, such as is available commercially for example as "Renographin 76®". FEP Teflon® has a refractive index about 1.33, and Renographin 76® has a refractive index about 1.46; the ratio of their refractive indices is thus about 1.1, providing for substantially total internal reflection even at fairly steep angles of incidence. Preferably the lumenal surface of the tube is smooth, as irregularities in the surface can introduce unsatisfactory irregularities in angles of incidence. Preferably the tube has a circular cross-sectional shape, and the inner diameter (i.e. the diameter of the lumen of the tube) is about 1–3 mm according to the diameter of the arterial lumen to be opened. Preferably the thickness of the wall 16 is at least about two times the wavelength of the transmitted light. Such a tube, 110 cm long, with a wall of FEP Teflon® and containing Renographin 76®, can transmit from the distal end about 60% of laser energy at 480 nm, launched through a refractive index-matched lens or window into the distal end from a laser.

Alternatively, the laser energy can be launched into a conventional quartz fiber from the laser, and the quartz fiber can be inserted into the proximal end of the tube. However, proximal portions of the tube which contain such a fiber are thereby rendered much less flexible, and it is advantageous in applications where great flexibility is required particularly in a distal portion of the light guide not to insert the fiber so far that the distal end of the fiber reaches into the preferably flexible distal region of the light guide.

Such a tube of such composition can have a "memory"; that is, the tube can be preformed to conform to a particular desired curvature, so that, while it can be straightened or flexed, it will tend to conform to a particular anatomical course corresponding to the preform curvature.

Figures 10, 11:
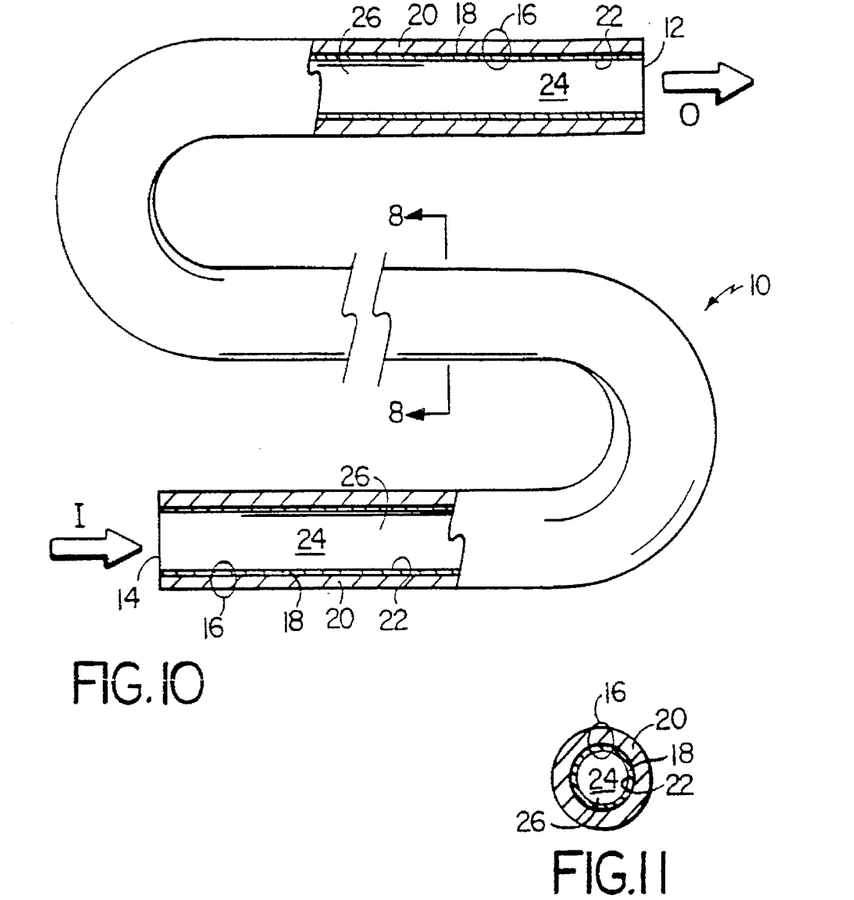
FIG. 10 is a somewhat diagrammatic view of portions of an alternate liquid core light guide of the invention, partially cut away along the long axis of the tube.
FIG. 11 is a section thru the light guide of FIG. 7 at 8—8.

Some materials that are optically suitable for use as a tube wall are structurally unsuitable or less suitable; that is, they are insufficiently flexible, or they collapse or kink or otherwise are distorted when they are bent through curves of small radius. FIGS. 10 and 11 show an alternate construction for the tube, in which the tube 16 includes inner wall layer 18, whose inner surface defines the lumenal surface 22 of the tube wall 16, and outer supportive layer 20. Inner wall layer 18, situated adjacent the lumen 24 of tube 10, is constructed of material having suitable optical characteristics, as described above with reference to FIGS. 1 and 2. Outer wall layer 20, which can be bonded to inner wall layer 18 or coextruded with it, is formed of material having suitable mechanical properties, so that tube wall 16 has structural strength as well as flexibility, as described above generally with reference to FIGS. 1 and 2.

The laser light guide operates generally as follows. With specific reference to its use for ablating arterial plaque occluding a coronary artery. Tube 10 is filled with liquid 26, and a source of laser energy is coupled to the distal end 14 of the liquid-filled tube. Fluid-filled tube 17 is introduced proximal end first through an opening in the skin and through the wall of a large artery such as the femoral artery, and is then passed translumenally toward the site of the occlusion to be treated by laser energy, until the distal end resides in the lumen of the occluded artery and is directed toward the occlusion. If the liquid is a radiographic contrast medium such as Renographin 76®, the progress of the tube toward the site can be followed by x-ray without interruption either with or without use of a guide wire. Once the proximal tip has reached the site and is directed toward the target, a further quantity of liquid can be introduced into the tube from a liquid source, causing some liquid to emerge (i.e. flow) from the proximal end of the tube toward the target. Blood situated between the tube and the target can interfere with laser ablation of the plaque, because the blood absorbs nearly all wavelengths of laser energy better than does plaque. The liquid passing from the distal end of the tube displaces blood between the tube and the target removing this interference. As the emerging liquid displaces the blood, it provides a liquid channel proximal to the proximal end of the tube for passage of laser energy to the target. Moreover, the index of refraction of blood is about 1.34, sufficiently low relative to that of the liquid that the blood surrounding the liquid in this channel forms an effective light guide between the distal end of the tube and the target. Such a temporary liquid-core, liquid-clad light channel can be effective over distances in the order of about a centimeter for time intervals generally sufficient in the usual circumstance to complete the ablation and open the arterial lumen.

Then the laser energy source is activated to produce laser energy having the desired wavelength and pulse duration and intervals. The progess of the laser ablation of the target can be observed by x-ray, as the liquid serves not only as a light guide component but also as a radiologic contrast medium. When the ablation has been completed, the liquid-filled tube is withdrawn.

A guide wire can be used in the above-described procedure as desired, for example, if the walls of the arteries to be traversed by the tube themselves contain plaque formations that would interfere with the passage of the proximal end of the tube during insertion. The guide wire traverses the liquid-filled lumen of the tube. A preformed tube as described above follows the course of the guide wire during insertion; once the tube is emplaced the guide wire can be removed, and the tube then conforms to its curving course through the arteries.

Figure 4:
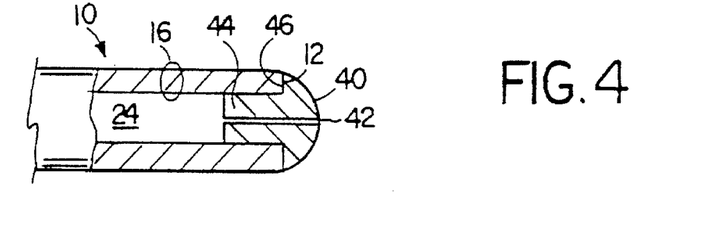
FIGS. 4 through 7 and 9 are somewhat diagrammatic views of the distal portion of a liquid core light guide, cut away along the long axis of the tube, showing end caps in various configurations.

Alternatively, as shown in FIGS. 4 through 9, the distal end of the tube can be provided with an end cap, to inhibit flow of liquid out from the distal end. With reference to FIG. 4, end cap 40 has generally cylindrical portion 44 whose diameter is such that portion 44 can be press fitted into tube 10; and an end portion 45 forming a shelf 46 that abuts proximal tube end 12. A hole 52 runs through the center of end cap 40, situated so that it is aligned with the long axis of tube 10 when end cap 40 is in place. Hole 52 has a diameter sufficiently large to permit passage of a guide wire. Where desired hole 52 can be made with a diameter sufficiently small that the flow of the liquid out from the distal end of the tube is restricted under conditions of use. For standard guide wires, and for aqueous liquids, a diameter about 500 microns can be suitable. End portion 45 is shaped to provide a smooth and rounded distal surface, so that the light guide can be easily passed distally to the site without becoming caught or damaging the vessel wall.

Figure 5:
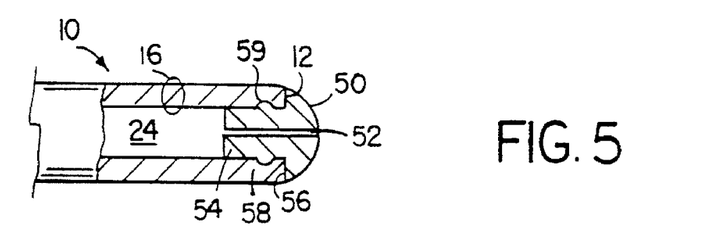
Figure 6:
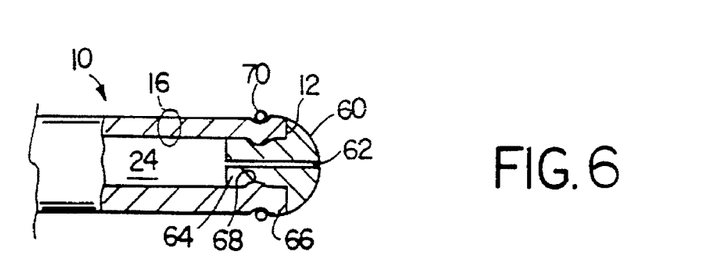

FIGS. 5 and 6 show alternative end caps 50 and 60, adapted to be more securely fastened to the distal end of tube 10. Generally cylindrical protion 54 of end cap 50 includes annular ridge 58, and tube 10 is provided near end 12 with annular groove 59 into which annular ridge 58 fits when end cap 50 is seated with shelf 56 of end portion 55 in abutment with tube end 12. Generally, cylindrical portion 64 of end cap 60 includes annular groove 68. End cap 60 is press fitted into tube 10 so that shelf 66 of end portion 66 abuts tube end 12, and then retaining ring 70 is placed about tube 10, compressing an annular portion of wall 16 into groove 68. End caps 50 and 60 are provided with holes 52 and 62 corresponding to hole 42 in end cap 40 as described above with reference to FIG. 4.

Figure 7:
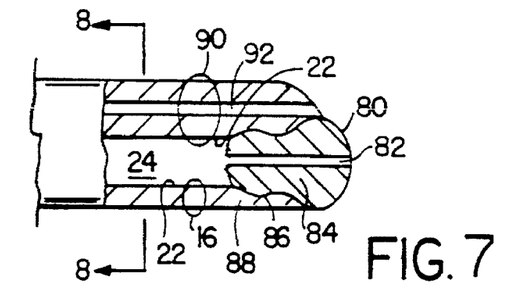
Figure 8:
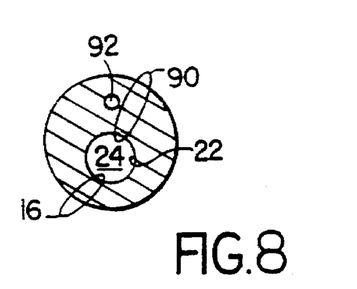
FIG. 8 is a section thru the distal portion of a liquid core light guide of FIG. 7 at 8—8.

FIGS. 7 and 8 show an alternate embodiment of a liquid core light guide of the invention, in which a passage for the guide wire is provided separate from the lumen containing the laser energy conducting liquid. Tube wall 16 is provided with a lumen 24 bounded by lumenal surface 22 similar to that described above with reference to FIGS. 1 through 3. 10 and 11, in which the liquid is located. A thickened portion 90 of wall 16 is provided with a longitudinal bore 92 through which a guide wire can pass. End cap 80 having a generally cylindrical portion 84 is press fitted or heat welded into the proximal end 88 of the tube. Generally cylindrical portion 84 of cap 80 is provided with an annular swelling 86, which conforms to the inner surface of the tube wall to form a secure attachment when the cap is assembled into the tube. End cap 80 can be provided with generally axially situated hole 82, if it is desired to permit a flow of liquid out from the proximal end of the tube. Alternatively, if no hole is provided in end cap 80, then end cap 80 provides a seal for preventing a flow of the liquid out from the tube, as may be desired for example if the liquid is corrosive to the surroundings near the site to be treated by the laser energy; or if the liquid is toxic or otherwise not biocompatible, as may be a concern in a medical application. Many liquids that are suitable for UV or for IR laser transmission, as generated for example by excimer, Holmium, or Erbium YAG lasers, are toxic or nonbiocompatible, while many radiographic contrast media transmit UV or far IR wavelengths only poorly.

Figure 9:
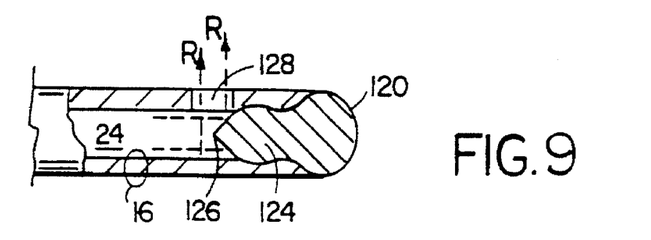

FIG. 9 shows an alternative construction for the cap, whereby the cap provides a reflective surface to direct the laser energy out through the tube wall in a direction away from the axis of the tube. End cap 120 is affixed generally as described above into the distal end of the tube. The proximal end of generally cylindrical portion 124 of cap 120 is provided with a reflective surface 126, which is shaped and oriented so that it reflects the laser energy in a desired direction, such as for example a direction generally perpendicular to the tube axis, as shown at arrows R in FIG. 9. A side hole 128 can be provided in wall 16 in the area where the light reflected from reflective surface 126 as at arrows R passes through the wall, to allow fluid to pass out from the tube toward a site situated lateral to the tube. This flow of fluid displaces blood in the zone between the tube wall and the target site, providing a temporary liquid-core, liquid-clad light guide as described above for conducting the laser energy to the target.

Alternatively, a window can be affixed within hole 128 of wall 16, made of, for example, quartz or sapphire, which is transparent to the reflected light but does not allow passage of the liquid. Such a window can prevent leakage of the liquid into the site, and can be desirable where, for example, the liquid is itself toxic or otherwise nonbiocompatible; or, in industrial applications, where the liquid is incompatible with the materials at the site.

As desired, the reflective surface 126 can be planar, or can be curved such that it causes the reflected laser energy to diverge or converge.

The end cap can be formed for example of quartz or of fused silica by for example end-melting a length of quartz or fused silica capillary tube having appropriate dimensions. The cap material can be optically matched with the liquid, such that, for example, the liquid and the cap have nearly the same index of refraction, and the interface between the liquid and the cap is not seen by the passing laser energy. If a cap is provided with a reflective surface, for example as described above with reference to FIG. 9, then the cap can have an index of refraction sufficiently different from that of the liquid to provide reflection at the interface, or the reflective surface can be provided with a reflective film or coating.

Figure 12:
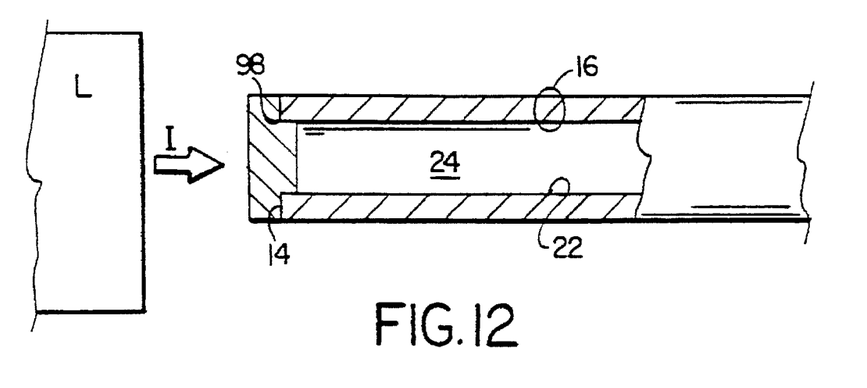
FIG. 12 partially cut away through the long axis of the tube, showing a window for coupling a source of laser energy to the light guide.

The light guide can be coupled to the source of laser energy by means known in the art of laser light guides. FIG. 12 shows a window 98 affixed to the distal end 14 of the tube. The laser energy is directed as shown generally by arrow I in a direction generally coaxial with the tube lumen 24 from a laser energy source, a portion of which is indicated diagrammatically at L, toward window 98, through which it passes into the tube lumen 24. Such a window can be made for example of quartz or fused silica having an index of refraction matched with that of the liquid, so that the interface between the liquid and the window is not seen by the passing laser energy.

Figures 13, 14:
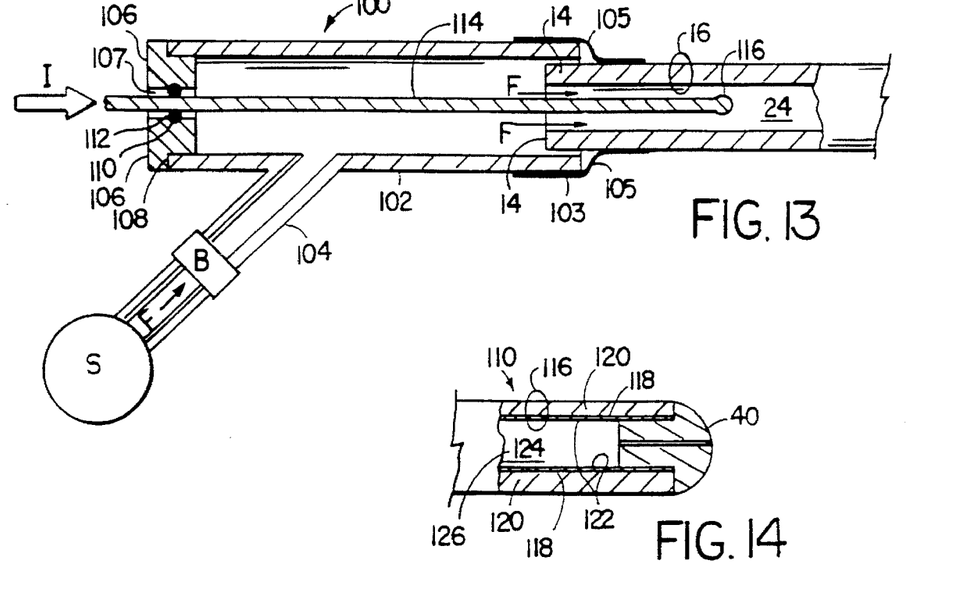
FIG. 13 partially cut away through the long axis of the tube, showing an alternate laser coupler employing an optical fiber.
FIG. 14 is a somewhat diagrammatic view of the proximal portion of an alternative liquid core light guide of the invention, cut away along the long axis of the tube, having a reflective lumenal surface.

An alternative coupler is shown in FIG. 13. This coupler can be used to launch the laser energy into the light guide from a conventional optical fiber that is conventionally coupled to the source of laser energy, and the coupler provides a Y connector shown generally at 100 through which the liquid can be introduced while the light guide is in use. Y connector 100 includes a generally cylindrical barrel 102 having an end 103 configured to fit over the proximal end 14 of the tube. A seal is established between barrel 102 and tube end 14 by heat-shrinking a length of tubing material 105 over the joint. Conduit 104 projects from barrel 102, to provide for introduction of liquid from a source of liquid, indicated diagramatically at S, into coupler 100 and lumen 24 of the tube. A conventional bubble filter, indicated generally at B, is interposed across the flow of liquid indicated generally at F, for preventing introduction of gas bubbles into the lumen 24 of the tube. Proximal end 108 of coupler 100 is affixed with a cap 106, which is provided with bore 107 through which conventional optical fiber 114 can pass. Distal cap 106 is provided with annular groove 110, which accommodates O-ring 112 to provide a seal between proximal cap 106 and fiber 114. Fiber 114, which can be provided with a conventional ball tip 116, is advanced proximally into lumen 24 of the tube as far as is desired. Because fiber 114 is insufficiently flexible to pass through a course having curves of small radius, fiber 114 should not be advanced distally beyond portions of the tube where such bends are not likely to be encountered. Preferably, ball tip 116 is advanced only as far as point outside the body into which the light guide is to be passed, so that the launch point between the fiber tip and the liquid can be inspected through the tube wall while the light guide is in use.

Where the optical fiber has a diameter between about 300 and 600μ, and the lumenal diameter of the tube is greater, as for example about 1–3 mm, liquid can flow as indicated generally by arrows F within the tube about the fiber while it is being introduced and once it is in place. The inserted fiber confers increased rigidity upon the tube, leaving a distal portion of the tube, into which the fiber does not reach, flexible; in many applications, such as, for example, laser irradiation of a coronary artery, this distal portion of the tube is the portion requiring the greatest flexibility.

Preferably the fiber is inserted so that its tip rests in a relatively straight portion of the tube, and with the fiber placed as nearly coaxially as possible to provide launch of the energy from the fiber tip as nearly coaxially with the tube as possible. A centering device at the tip of the fiber can help to maintain the coaxial relationship; and a fiber made, for example, of a quartz having a low index of refraction can be used to help direct the light principally in a longitudinal direction at the point of launch, PL (i.e. the point at which the laser energy passes out of the distal end of the fiber 114 and into the liquid within the distal portion of the lumen 124).

In an alternative embodiment, shown in FIG. 14, the light guide includes a tube, shown generally at 110, whose wall 116 encloses a lumen 124 which is filled with liquid 126.

Wall 116 includes outer layer 120, and inner layer 118. Inner layer 118 has a reflective surface defining lumenal surface 122 of tube 110. Inner layer 118 can be made of a metallized materials containing, for example, aluminum or silver; or inner layer 118 can be made of a reflective polymer. Outer layer 120 is formed of material having suitable mechanical properties, so that tube wall 116 has structural strength as well as flexibility, as described above generally with reference to FIGS. 1 and 2 and FIGS. 10 and 11. A tube made of such materials and filled with liquid can be bent through curves of small radius without kinking or substantially distorting the cross-sectional geometry of the tube, and can work as a light guide for delivery of laser energy.

Figure 15:
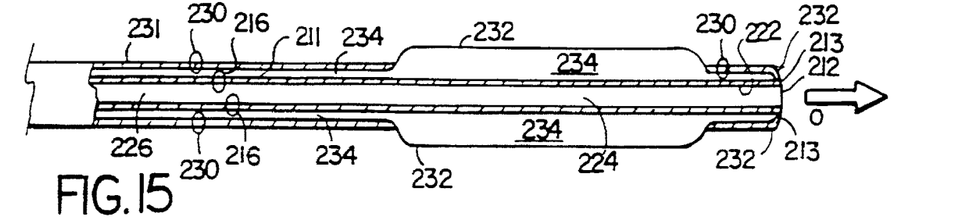
FIG. 15 is a somewhat diagrammatic view of the distal portion of a liquid core light guide of the invention, cut away along the long axis of the tube, in combination with a balloon dilation device.

In an alternative embodiment, shown in FIG. 15, apparatus is shown generally at 210 combining a liquid filled light guide of the invention with a balloon catheter adapted to cooperate with the liquid light guide. The light guide includes a tube 211 whose wall 216 has a lumenal surface 222 surrounding a lumen 224 that can be filled with liquid 226. The wall 216 and the liquid 226 are selected as described above with reference to FIGS. 1 and 2 to have optical characteristics such that the liquid 226 and the wall 216 together from a liquid core light guide; laser energy directed into the proximal end (not shown in FIG. 15) of liquid filled tube 211 passes within lumenal space 224 toward distal end 212 of tube 211 from which a portion of the light emerges, as indicated generally by arrow O. Tube 211 is contained in generally coaxial relation within a catheter tube 230 so that a space 234 is contained between catheter wall 230 and tube wall 216. Distal tube end 212 is affixed to proximal end 232 of catheter 231 in annular sealed relation at 213. As in a conventional balloon dilation catheter, catheter wall 230 includes an expandable wall portion 232, so that when fluid is introduced under pressure into the space 234, the expandable portion 232 of wall 231 swells or inflates to a configuration such as that for example shown in FIG. 15.

Adaptation of a balloon dilation catheter and combination of it with a liquid core light tube as illustrated for example in FIG. 15 can be used for combination balloon/laser angioplasty as follows. The catheter, with the balloon deflated, containing the light tube can be inserted to the site where angioplasty is to be carried out, using a guide wire within the lumen of the light guide if desired. When the site to be treated, such as an atheroma, is reached, laser energy can be directed through the light guide onto the site to ablate a portion of the plaque to form a channel sufficient to permit passage of the catheter. Then the catheter can be inserted through the channel to bring the exandable balloon portion into the angioplasty site, and fluid can be introduced into the balloon to cause it to inflate and expand the blood vessel at the site as in cenventional balloon angioplasty. Finally the balloon can be deflated and the catheter removed.

Figure 16:
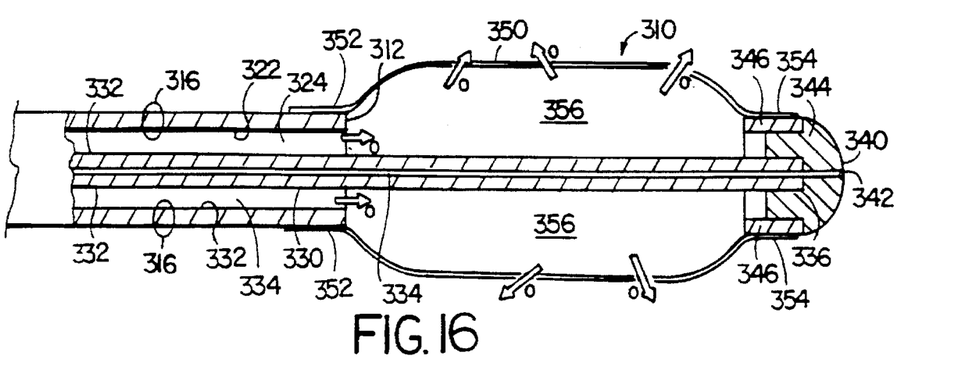
FIG. 16 is a somewhat diagrammatic view of the distal portion of a liquid core light guide of the invention, cut away along the long axis of the tube, showing a light diffusion balloon.

In another embodiment, shown in FIG. 16, an area of the lumenal surface of a vessel wall can be treated with diffuse light directed to the site through a liquid filled light guide according to the invention. In this embodiment the light guide includes a tube 316 constructed of a materials selected in part to provide a high degree of internal reflection at the lumenal surface 322 when tube. 316 is filled with a suitable liquid, and in part to provide structural strength and flexibility so that the liquid-filled light guide can be bent through curves of small radius without kinking or substantially distorting the cross-sectional geometry of the tube, as described above with reference to FIGS. 1 and 2 or FIGS. 10 and 11. Contained within tube 316 in generally coaxial relation is an inner tube 330 having bore 334 through which a conventional guide wire can be passed. Inner tube 330 is constructed of materials selected also in part to provide a high degree of reflection at the outer surface 332 when tube 316 is filled with a suitable liquid 326, and in part to be strong and flexible. Affixed to the distal end 336 of inner tube 330 is an end cap 340 having bore 342 aligned with inner tube bore 334, through which a conventional guide wire can pass. End cap 340 is generally similar to end caps described above with reference to FIGS. 4 through 6. A generally cylindrical portion 344 of end cap 340 is affixed to a flange 346, which can be constructed of the same material as tube 316. An expandable sleeve 350, of a material transparent to the light to be delivered to the site, is affixed in annular sealed relation at one end 352 to the distal end 312 of tube 316 and at the other end 354 to the distal end of flange. 346, so that sleeve 350 forms a transparent portion of the wall of the light tube surrounding a space 356 proximal to the tube end 312.

A conventional balloon angioplasty generally produces a dilated portion of the vessel in which the lumenal surface contains cracks and fissures. These cracks and fissures fill with blood and other matter contained within the vessel. Often, after a time, this matter disperses or is dislodged from the cracks and fissures, and the dilated portion of the vessel collapses, forming a restenosis at the angioplasty site. The matter can be caused to remain in the cracks for a greater time, delaying the collapse of the vessel and the restenosis, by denaturing the material, for example by application of heat, so that the material forms in effect a mortar in the cracks. The matter can be heated and denatured by, for example, irradiating the dilated vessel wall with diffuse light energy.

A liquid filled light guide constructed according to the invention and having a transparent wall portion as illustrated for example in FIG. 16 can be used to provide such an irradiation of the inner wall of a vessel following balloon angioplasty as follows. Following balloon angioplasty the balloon catheter is withdrawn, and, while the cracks and fissures are still filled with matter, the liquid filled light guide is inserted, over a guide wire if desired, so that the transparent portion of the wall of the light guide rests within the dilated portion of the vessel. Then further liquid is introduced under pressure through the lumen 324 of the light guide, expanding the expandable transparent wall portion 350 within the dilated portion of the vessel. Then light is directed through the lumen 324 of the light guide from the distal end (not shown in FIG. 16) toward the proximal end 312, from which a portion of the light emerges into the liquid-filled space 356, as indicated generally by arrows O. Because the light can pass outward through expandable transparent wall portion 350, the light is not guided lengthwise in the portion of the tube surrounding liquid-filled space 356, and the light leaks outward diffusely from the tube through transparent expanded wall portion 350, as indicated generally by arrows D. The leaking light can then be .absorbed by the lumenal portions of the vessel wall surrounding the expanded portion 350 of the light guide, where the light can denature the matter that has collected in the cracks and fissures of the inner vessel wall, having the effect of mortaring the wall and helping to prevent its collapse.

Other Embodiments

Other embodiments are within the following claims. For example, the liquid and the material of the inner wall of the light guide can be selected from any of a variety of materials, provided the tube wall has suitable mechanical properties and provided the indices of refraction of at least an inner layer of the wall and of the liquid differ relatively so that they cooperate to provide a light guide effect. The liquid and the inner wall material preferably are selected to maximize the ratio of the indices of refraction of the liquid and of the inner wall of the tube. Where the wall material has been selected, the index of refraction of the liquid must be at least as high as that of the selected wall material; and, conversely, where the liquid has been selected, the index of refraction of the inner wall material must be lower than that of the selected liquid, as discussed generally above.

Where a flow of the liquid into the milieu beyond the proximal end of the light guide is employed to provide a temporary liquid-core, liquid-clad light guide between the proximal end of the tube and the target site, the selected liquid must have an index of refraction greater than that of the milieu. The liquid can be introduced into the tube by means, for example, of a syringe or of a pump, such as for example a peristaltic pump, configured and arranged so that it is capable of providing a flow of fluid without introducing air bubbles into the tube. Preferably where the means for providing the flow of fluid is capable of producing high pressures, conventional means are provided for shutting off the flow when the pressure exceeds a level of safety.

Any of a variety of radiographic contrast media can be used, including a nonionic contrast medium such as, for example, contrast media commercially available as Hexabrix® or Omnipaque®, or an ionic contrast medium such as, for example, contrast media commercially available as Renographin 76®, or Angiovist®.

Admitting a fiber into the light guide will make much less flexible that portion of the light guide containing the fiber; in circumstances where great flexibility is needed principally in a distal portion of the catheter, such as, for example, where the site to which the laser energy is to be delivered is in a coronary artery, the fiber can be admitted only as far as a point proximal to the distal portion of the tube in which great flexibility is required. This can provide for a straightforward launch of energy into the liquid light guide, and can shorten the distance within the liquid light guide through which the energy is transmitted, thereby reducing losses and increasing the transmission efficiency of the delivery apparatus.

We claim:

1. A flowing fluid laser catheter system for transmitting laser energy from an extracorporeally located laser generating device to a mass of target matter located within a mammalian body, said catheter system comprising:

a flexible catheter body having a proximal end, a distal end, an outer surface and a luminal surface, the luminal surface of said catheter body defining a fluid flow lumen which extends longitudinally through at least a portion of said catheter body, said fluid flow lumen having a first diameter;

a laser transmitting optical fiber extending longitudinally through a proximal portion of said fluid flow lumen, said optical fiber having a proximal end, a distal end and an outer surface, said optical fiber having a second diameter which is smaller than the first diameter of said fluid flow lumen, the distal end of said optical fiber being disposed within said fluid flow lumen a spaced distance proximal to the distal end of said catheter body, with said outer surface of said optical fiber not contacting the luminal surface, thereby providing a generally annular fluid flow space which laterally surrounds said optical fiber;

a fluid inflow opening formed in said catheter body at a location proximal to the distal end of said optical fiber to permit infusion of a laser transmitting liquid into said fluid flow lumen;

a fluid outflow opening formed in said catheter body at location distal to and in alignment with the distal end of said optical fiber;

a flow of laser transmitting liquid being infused in the distal direction through said fluid inflow opening, through said generally annular flow space and out of said fluid outflow opening, concurrently with the transmission of laser energy through said optical fiber such that said laser energy is launched from the distal end of said optical fiber into the flow of laser transmitting liquid and is carried within said flow of laser transmitting liquid out of said fluid outflow opening and into contact with said target matter.

2. The flowing fluid laser catheter of claim 1 wherein the optical fiber is coaxially centered within the fluid flow lumen of said catheter body.

3. The flowing fluid laser catheter of claim 2 further comprising:

a centering apparatus for holding said optical fiber in a substantially coaxially centered position within said fluid flow lumen.

4. The flowing fluid laser catheter of claim 1 wherein said second diameter of said optical fiber is about 1–3 mm.

5. The flowing fluid laser catheter of claim 1 further comprising:

a Y-connector positioned on the proximal end of said catheter body, said Y-connector having a first furcation through which said optical fiber is inserted, and a second end and a second furcation forming said liquid inflow opening through which said laser transmitting liquid is infused.

6. The flowing fluid laser catheter of claim 1 further comprising:

a bubble filter connected to said catheter lumen for filtering gas bubbles from said laser transmitting liquid.

7. The flowing fluid laser catheter system of claim 1 wherein:

said luminal surface has a refractive index $N_w$;

said laser transmitting liquid has a refractive index $N_f$; and the refractive index ($N_f$) of said laser transmitting liquid being greater than the refractive index of said luminal surface ($N_w$).

8. The flowing fluid laser catheter system of claim 7 wherein the ratio of said refractive index of said liquid $N_f$ to the refractive index of said luminal surface $N_w$ is greater than 1.0.

9. The flowing fluid laser catheter system of claim 7 wherein the ratio of said refractive index of said liquid $N_f$ to the refractive index of said luminal surface $N_w$ is greater than 1.05.

10. The flowing fluid laser catheter system of claim 7 wherein the ratio of said refractive index of said liquid $N_f$ to the refractive index of said luminal surface $N_w$ is greater than 1.10.

11. The flowing fluid laser catheter of claim 7 wherein the value of $N_f$ is at least about 1.46.

12. The flowing fluid laser catheter of claim 7 wherein the value of $N_w$ is at least about 1.33.

13. The flowing fluid laser catheter of claim 1 wherein the luminal surface of said fluid flow lumen is formed of fluorinated ethylenepropylene.

14. The flowing fluid laser catheter of claim 1 wherein the luminal surface of said fluid flow lumen is formed of fluorinated polypropylene.

15. The flowing fluid laser catheter system of claim 1 wherein at least a portion of said fluid flow space between said luminal surface and said optical fiber is sufficiently large to permit passage of a guide wire therethrough, next to said optical fiber.

16. The flowing fluid laser catheter of claim 1 further comprising:
   a guide wire passage lumen extending longitudinally through said catheter body to permit passage of a guide wire therethrough, said guide wire passage lumen being formed separately from said fluid flow lumen.

17. The flowing fluid laser catheter of claim 1 wherein said first diameter of said fluid flow lumen is about 1–3 mm and wherein said fluid outflow aperture has a diameter of about 500 microns.

18. The flowing fluid laser catheter of claim 1 wherein said luminal surface comprises a reflective layer.

19. The flowing fluid laser catheter of claim 18 wherein said reflective layer is bonded to said luminal surface.

20. The flowing fluid laser catheter of claim 18 wherein said reflective layer comprises a metallized layer.

21. The flowing fluid laser catheter of claim 1 wherein the portion of said catheter which extends distally beyond the distal end of said optical fiber is bendable into a curve having a radius of curvature of 20 mm without substantial change in the cross sectional shape of said catheter body.

22. The flowing fluid laser catheter of claim 1 wherein the portion of said catheter which extends distally beyond the distal end of said optical fiber is bendable into a curve having a radius of curvature of 10 mm without substantial change in the cross-sectional shape of said catheter body.

23. A laser catheter system comprising the flowing fluid laser catheter of claim 1 further in combination with a laser generating device coupled to the proximal end of said optical fiber.

24. The laser catheter system of claim 23 wherein said laser generating device is a pulse dye laser.

25. The laser catheter system of claim 23 wherein said laser generating device is an excimer laser.

26. The flowing fluid laser catheter system of claim 23 wherein said laser generating device is an Holmium laser.

27. The flowing fluid laser catheter system of claim 23 wherein said laser generating device is an Erbium YAG laser.

28. The flowing fluid laser catheter of claim 1 further comprising:
   a dilation balloon positioned on the outer surface of said catheter body; and
   a balloon inflation fluid channel extending through said catheter body for passing balloon inflation fluid into and out of said balloon.

* * * * *